United States Patent [19]

Jeppesen

[11] Patent Number: 5,741,785
[45] Date of Patent: Apr. 21, 1998

[54] HETEROCYCLIC COMPOUNDS, THEIR PREPARATION AND USE

[75] Inventor: Lone Jeppesen, Virum, Denmark

[73] Assignee: Novo Nordisk A/S, Bagsvaerd, Denmark

[21] Appl. No.: 385,250

[22] Filed: Feb. 8, 1995

[30] Foreign Application Priority Data

Feb. 11, 1994 [DK] Denmark .................. 0183/94
Nov. 25, 1994 [DK] Denmark .................. 1351/94

[51] Int. Cl.$^6$ .............. A61K 31/675; A61K 31/495; C07F 9/576; C07D 487/04
[52] U.S. Cl. .............. 514/81; 514/250; 544/337; 544/346
[58] Field of Search .............. 544/337, 346; 514/81, 250

[56] References Cited

U.S. PATENT DOCUMENTS 4,291,033  9/1981  Barnes et al. .................. 544/346
5,153,196  10/1992  McQuaid .................. 514/250

FOREIGN PATENT DOCUMENTS

| 0 400 583 | 12/1990 | European Pat. Off. . |
| 43 10523 | 10/1994 | Germany . |
| 43 29970 | 10/1994 | Germany . |
| 2043064 | 10/1980 | United Kingdom . |
| 2043637 | 10/1980 | United Kingdom . |
| WO 93/04066 | 3/1993 | WIPO . |
| 94-22865 | 10/1994 | WIPO .................. 544/346 |

OTHER PUBLICATIONS

Ager et al., J. Med. Chem., vol. 31, pp. 1098–1115 (1988).
D.D. Davey et al., J. Med. Chem., vol. 34, pp. 2671–2677 (1991).
McQuaid et al., J. Med. Chem., vol. 35, pp. 3319–3324 (1992).
Jackson et al., Bioorg. Med. Chem. Lett., vol. 1, No. 12, pp. 751–756 (1991).

*Primary Examiner*—Emily Bernhardt
*Attorney, Agent, or Firm*—Steve T. Zelson; Elias J. Lambiris

[57] ABSTRACT

Imidazo[1,2-a]quinoxalinone derivatives of the general formula

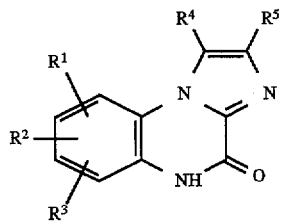

wherein $R^1$, $R^2$, $R^3$ are the same or independently are H, alkyl, alkoxy, halogen, $NO_2$, $NH_2$, $CF_3$, CN, $SO_2CH_3$, $SO_2CF_3$, $SO_2NR'R''$ or a 5- or 6-membered N-containing heterocyclic ring, optionally substituted, and R', R'' are independently H or alkyl; and $R^4$ is H or $CH_2$-$R^6$; and $R^6$ is H, halogen, $POR'''R''''$, $NR^7R^8$ or a 5- or 6-membered N-containing heterocyclic ring optionally substituted, and R''', R'''' are independently hydroxy or alkoxy; and

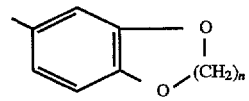

$R^7$, $R^8$ are the same or independently are H, or alkyl optionally substituted; and n is 1, 2 or 3;

$R^5$ is

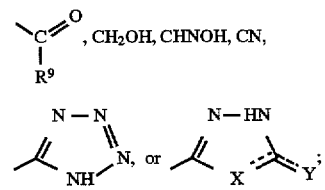

and $R^9$ is OH, alkoxy, H or $NR^{10}R^{11}$; and $R^{10}$, $R^{11}$ are the same or independently are H, $NH_2$ or OH; and X is O or S; and Y is O, S or $NH_2$, and pharmaceutically acceptable salts thereof, have affinity for the AMPA receptors and are antagonists in connection with this type of receptor which makes them useful in the treatment of CNS ailments, especially in the treatment of any of the numerous indications caused by hyperactivity of excitatory amino acids.

38 Claims, No Drawings

HETEROCYCLIC COMPOUNDS, THEIR PREPARATION AND USE

The present invention relates to therapeutically active heterocyclic compounds, a method of preparing the same, pharmaceutical compositions comprising the compounds, and a method of treating therewith.

More specifically, the invention relates to novel imidazo[1,2-a]quinoxalinone derivatives which are useful in the treatment of any indication caused by hyperactivity of excitatory amino acids, especially neuronal degeneration as are observed in amyotrophic lateral sclerosis, Huntington's chorea, Parkinson's disease, epilepsy and senile dementia or mental and motor dysfunctions seen after conditions of brain ischemia, oxygen deficiency, hypoglycemia and head and spinal cord trauma. Other possible indications are psychosis, muscle rigidity, emesis, acute and chronic inflammatory disease and analgesia.

L-glutamic acid, L-aspartic acid and a number of other closely related amino acids have in common the ability to activate neurons in the central nervous system (CNS). Biochemical, electrophysiological and pharmacological studies have substantiated this and demonstrated that acidic amino acids are transmitters for the vast majority of excitatory neurons in the mammalian CNS.

Interaction with glutamic acid mediated neurotransmission is considered a useful approach in the treatment of neurological and psychiatric diseases. Thus, known antagonists of excitatory amino acids have shown potent anxiolytic (Stephens et al., Psychopharmacology 90, 143–147, 1985), anticonvulsant (Croucher et al., Science 216, 899–901, 1982) and muscle relaxant properties (Turski et al., Neurosci. Lett. 53, 321–326, 1985).

It has been suggested that accumulation of extracellular excitatory amino acids, followed by overstimulation of neurons, may explain the neuronal degenerations seen in neurological disorders such as amyotrophic lateral sclerosis, Parkinsonism, Alzheimer's disease, Huntington's disease, epilepsy, and deficiencies of mental and motor performance seen after conditions of brain ischemia, anoxia and hypoglycemia or head and spinal cord trauma (McGeer et al., Nature 263, 517–519, 1976; Simon et al., Science 226, 850–852, 1984; Wieloch, Science 230, 681–683, 1985; Faden et al., Science 244, 798–800, 1989; Turski et al., Nature 349, 414–418, 1991). Other possible indications are psychosis, muscle rigidity, emesis, acute and chronic inflammatory disease (Pluka et al., Neurosci. Lett. 149, 99–102, 1933) and analgesia (Hao et al., J. Pharm. ExoTher. 267, 140–144, 1993; Dykstra et al., Neuroreport, 4, 879–882, 1993).

Excitatory amino acids exert their actions via specific receptors located postsynaptically or presynaptically. Such receptors are at present conveniently subdivided into three groups bases on electrophysiological and neurochemical evidence: 1 the NMDA (N-methyl-D-aspartate) receptors, 2 the AMPA receptors, and 3 the kainate receptors. L-glutamic acid and L-aspartic acid probably activate all the above types of excitatory amino acid receptors and possibly other types as well.

The above mentioned classification of excitatory amino acid receptors into NMDA, AMPA, and kainate receptors is based primarily on the following electrophysiological and neurochemical findings.

1) N-methyl-D-aspartate (NMDA) receptors exhibit high selectivity for the excitant NMDA. Ibotenic acid, L-homocysteic acid, D-glutamic acid and trans-2,3-piperidine dicarboxylic acid (trans-2,3-PDA) exert a strong to moderate agonist activity on these receptors. The most potent and selective antagonists are the D-isomers of the 2-amino-5-phosphonocarboxylic acids, e.g. 2-amino-5-phosphono-valeric acid (D-APV) and 3-[(±)-2-carboxy-piperazin-4-yl]-propyl-1-phosphonic acid (CPP), while moderate antagonist activity is shown by the D-isomers of long chain 2-amino dicarboxylic acids (e.g. D-2-aminoadipic acid) and long chain diaminodicarboxylic acids (e.g. diaminopimelic acid). The NMDA-induced synaptical responses have been extensively investigated in the mammalian CNS, especially in the spinal cord (J. Davies et ah, J. Physiol. 297, 621–635, 1979) and the responses have been shown to be strongly inhibited by $Mg^{2+}$.

2) AMPA receptors are activated selectively by AMPA (2-amino-3-hydroxy-5-methyl-4-isoxazolepropionic acid), other potent agonists being quisqualic acid and L-glutamic acid. Glutamic acid diethyl ester (GDEE) is a selective but very weak antagonist of this site. AMPA receptors are relatively insensitive to $Mg^{2+}$.

Glutamate release has long been thought to play a major role in neuronal death resulting from cerebral ischemia (Benveniste, H. et al., J. Neurochem. 43, 1369–1374, 1984). It is well known that NMDA receptor evoked $Ca^{2+}$ influx is an important mechanism in ischemic neuronal cell loss. The non-NMDA receptor coupled ionophor is not permeable to calcium. However, the excitation by the Scaffer collaterals in the CA1 region is excerted by non-NMDA receptors, and this fact is of importance for the events in the postischemic period. Recent studies have shown that selective AMPA antagonists have neuroprotectant effects in global ischemia in the gerbil even when given several hours after reperfusion (Sheardown et al., Science 247, 571–574, 1990).

AMPA antagonists are therefore useful in the treatment of cerebral ischemia.

3) Kainate receptors. Excitatory responses to kainic acid are relatively insensitive to antagonism by NMDA-antagonists and by GDEE, and it has been proposed that kainic acid activates a third subclass of acidic amino acid receptor. Certain lactonized derivatives of kainic acid are selective antagonists (O. Goldberg et al., Neurosci. Lett. 23, 187–191, 1981) and the dipeptide 3-glutamyl-glycine also shows some selectivity for kainate receptors. Ca2+ but not $Mg^{2+}$ is a strong inhibitor of kainic acid binding.

Various related compounds are known from the prior art.

In GB-A-2043064 4-oxoimidazoquinoxaline derivatives substituted at the benzene ring with one or two of hydrogen or halogen and with an ester or a carboxylic acid group at position 2 are described and specifically, ethyl 4,5-dihydro-4-oxoimidazo[1,2-a]quinoxaline-2-carboxylate, 4,5-dihydro-4-oxoimidazo[1,2-a]quinoxaline-2-carboxylic acid, 7,8-dichloro-4,5-dihydro-4-oxoimidazo[1,2-a]quinoxaline-2-carboxylic acid and 7,8-dibromo-4,5-dihydro-4-oxoimidazo[1,2-a]quinoxaline-2-carboxylic acid are disclosed. However, these compounds are claimed to have anti-allergic activity and no indication of effect in the central nervous system is given.

In J. Med. Chem. 31, 1098–1115, 1988 the synthesis and oral anti-allergic activity of carboxylic acids derived from inter alia imidazo[1,2-a]quinoxalinones have been reported.

EP-A 0 400 583 generically describes inter alia a class of imidazoquinoxalin-4(5H)-ones optionally having lower alkyl, which may be substituted with different groups comprising nitrogen as the substituent at the imidazo ring. These compounds are claimed to possess inodilatory, vasodilatory or venodilatory effects.

Further, GB-A-2043637 generically describes a very broad class of pyrrolo- or imidazo-fused benzoxazine-, quinoxaline- or quinoline derivatives possibly with a keto group at position 4. Said compounds are alleged to have anti-allergic activity and no suggestion of activity in the central nervous system is given.

Furthermore, the synthesis and cardiovascular effects of a series of inter alia imidazo[1,2-a]quinoxalinones which are unsubstituted at the imidazo ring, are described in J. Med. Chem. 34, 2671–2677, 1991.

International patent publication No. WO 93/04066 discloses certain imidazoquinoxalinols substituted at position 2 in the imidazoring with phenyl, thienyl or pyridyl each of which is mono- or disubstituted. These compounds are claimed to be agonists, antagonists or inverse agonists for GABA brain receptors making them useful in the diagnosis and treatment of e.g. anxiety, sleep and seizure disorders.

In U.S. Pat. No. 5,153,196 some excitatory amino acid receptor antagonists and methods for the use thereof are described. The compounds conform inter alia to imidazoquinoxalin-4(5H)-ones, optionally having one substituent being alkyl, aromatic or $CF_3$ at the imidazo ring. However, the only imidazoquinoxalinone compound specifically disclosed is 7,8-dichloroimidazo[1,2-a]quinoxalin-4(5H)-one (37) and no documentation for its antagonistic effect is given in the specification.

Further, it has been reported in J. Med. Chem., 35, 3319–3324, 1992 that 7,8-dichloro-imidazo[1,2-a]quinoxaline-4(5H)-one (unsubstituted at the imidazo ring) possesses a reasonable affinity for the AMPA receptor.

Furthermore, in Bioorg. Med. Chem. Lett. 12, 751–756, 1991 the synthesis and affinity for glycine and AMPA of a series of tricyclo quinoxalines is described. Contrary to the compounds of the present invention the compounds mentioned in said reference are unsubstituted at the imidazo ring.

It has now been found that a novel class of substituted imidazo[1,2-a]quinoxalinone compounds have affinity for the AMPA and kainate receptors and are antagonists in connection with this type of receptors, which makes them useful in the treatment of any of the numerous indications caused by hyperactivity of excitatory amino acids and more specifically are observed in neuronal degeneration as are observed in amyotrophic lateral sclerosis, Huntington's chorea, Parkinson's disease, epilepsy and senile dementia or mental and motor dysfunctions seen after conditions of brain ischemia, oxygen deficiency, hypoglycemia and head and spinal cord trauma. Other possible indications are psychosis, muscle rigidity, emesis, acute and chronic inflammatory disease and analgesia.

Said class of compounds consists of compounds having the formula I

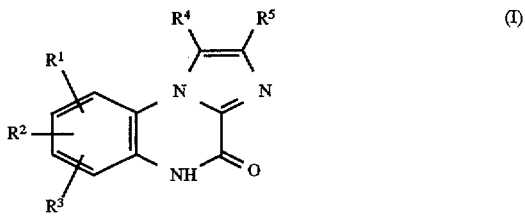

wherein $R^1$, $R^2$, $R^3$ are the same or independently are hydrogen, $C_{1-6}$-alkyl, $C_{1-6}$alkoxy, halogen, $NO_2$, $NH_2$, $CF_3$, CN, $SO_2CH_3$, $SO_2CF_3$, $SO_2NR'R''$ or a 5- or 6-membered nitrogen-containing heterocyclic ring, optionally substituted with phenyl or $C_{1-6}$-alkyl; and R', R'' are independently hydrogen or $C_{1-6}$-alkyl; and $R^4$ is hydrogen or $CH_2$-$R^6$; and $R^6$ is hydrogen, halogen, $POR'''R''''$, $NR^7R^8$ or a 5- or 6-membered nitrogen-containing heterocyclic ring optionally substituted with one or two of phenyl, $C_{1-6}$-alkyl or halogen; and R''' and R'''' are independently hydroxy or $C_{1-6}$-alkoxy; and $R^7$ $R^8$ are the same or independently are hydrogen,

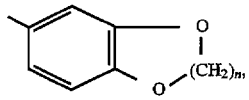

or $C_{1-6}$-alkyl optionally substituted with hydroxy or phenyl; and n is 1, 2 or 3;

$R^5$ is

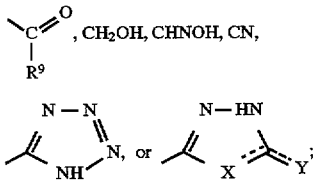

and $R^9$ is hydroxy, $C_{1-6}$-alkoxy, hydrogen or $NR^{10}R^{11}$; and $R^{10}$, $R^{11}$ are the same or independently are hydrogen, $NH_2$ or OH; and X is O or S; and Y is O, S or $NH_2$; and pharmaceutically acceptable salts thereof;

provided that when $R^4$ is hydrogen, $R^5$ is COOH or COOEt and one of $R^1$, $R^2$ or $R^3$ is hydrogen then the other two of $R^1$, $R^2$ or $R^3$ are not both hydrogen, Cl or Br.

The term "halogen" as used herein refers to Cl, Br, F and I, preferably Cl, Br and F.

The term "$C_{1-6}$-alkyl" as used herein refers to a straight or branched, saturated hydrocarbon chain having 1–6 carbon atoms such as methyl, ethyl, 2-propyl, isopropyl, 2-butyl, tert.butyl, 3-pentyl, neopentyl or n-hexyl.

The term "$C_{1-6}$-alkoxy" as used herein refers to a monovalent substituent comprising an $C_{1-6}$-alkyl group linked through an ether oxygen having its free valence bond from the ether oxygen, e.g. methoxy, ethoxy, propoxy, butoxy, pentoxy.

The term "5- or 6-membered nitrogen-containing heterocyclic ring" as used herein refers to a monocyclic unsaturated or saturated ring containing one or more nitrogen atoms and having 5 or 6 members, e.g. pyrrolidinyl, pyrrolinyl, imidazolidinyl, pyrazolidinyl, pyrazolinyl, piperidyl, piperazinyl, pyrrolyl, 2H-pyrrolyl, imidazolyl, pyrazolyl, triazolyl, pyridyl, pyrazinyl, pyrimidinyl, pyridazinyl, morpholino, thiomorpholino, isothiazolyl, isoxazolyl, oxazolyl, oxadiazolyl, thiadiazolyl, thiazolyl.

In a preferred embodiment of the invention, one of $R^1$, $R^2$ and $R^3$ is hydrogen, and the others of $R^1$, $R^2$ and $R^3$ are hydrogen, $C_{1-6}$-alkyl, preferably methyl, ethyl, isopropyl or tert.butyl, halogen, preferably Cl, Br or F, $NO_2$, CN, $CF_3$, $SO_2CH_3$, $SO_2CF_3$, imidazolyl, triazolyl, morpholino, benzimidazolyl, imidazolyl substituted with phenyl, or imidazolyl substituted with $C_{1-6}$-alkyl, preferably methyl or ethyl.

In another preferred embodiment of the invention $R^4$ is $CH_2$-$R^6$ wherein $R^6$ is hydrogen, halogen, preferably Cl, Br or F, dihydroxyphosphoryl, imidazolyl, imidazolyl substituted with $C_{1-6}$-alkyl, preferably methyl or ethyl, imidazolyl substituted once or twice with halogen, preferably chlorine, piperazinyl substituted with $C_{1-6}$-alkyl, preferably methyl or ethyl.

In another preferred embodiment of the invention $R^5$ is COOH, COOEt, CONH$_2$, CONHNH$_2$, CHO, CH$_2$OH, CH=NOH or oxadiazolthionyl.

Preferred compounds of the invention are:

2-Ethoxycarbonyl-1-methyl-7-trifluoromethylimidazo[1,2-a]quinoxalin-4(5H)-one;

2-Carboxy-1-methyl-7-trifluoromethylimidazo[1,2-a]quinoxalin-4(5H)-one;

1-Bromomethyl-2-ethoxycarbonyl-7-trifluoromethylimidazo[1,2-a]quinoxalin-4(5H)-one;

1-Bromomethyl-2-carboxy-7-trifluoromethylimidazo[1,2-a]quinoxalin-4(5H)-one;

2-Ethoxycarbonyl-1-(1-imidazolylmethyl)-7-trifluoromethylimidazo[1,2-a]quinoxalin-4(5H)-one;

2-Carboxy-1-(1-imidazolylmethyl)-7-trifluoromethylimidazo[1,2-a]quinoxalin-4(5H)-one;

2-Ethoxycarbonyl-1-(2-methyl-1-imidazolyl)methyl-7-trifluoromethylimidazo[1,2-a]quinoxalin-4(5H)-one;

2-Carboxy-1-(2-methyl-1-imidazolyl)methyl-7-trifluoromethylimidazo[1,2-a]quinoxalin-4(5H)-one;

1-(4,5-Dichloro-1-imidazolyl)methyl-2-ethoxycarbonyl-7-trifluoromethylimidazo[1,2-a]quinoxalin-4(5H)-one;

2-Carboxy-1-(4,5-dichloro-1-imidazolyl)methyl-7-trifluoromethylimidazo[1,2-a]quinoxalin-4(5H)-one;

2-Ethoxycarbonyl-1-(4-methyl-1-piperazinyl)methyl-7-trifluoromethylimidazo[1,2-a]quinoxalin-4(5H)-one;

2-Carboxy-1-(4-methyl-1-piperazinyl)methyl-7-trifluoromethylimidazo[1,2-a]quinoxalin-4(5H)-one;

2-Ethoxycarbonyl-1-(3,4-methylenedioxyanilino)methyl-7-trifluoromethylimidazo[1,2-a]quinoxalin-4(5H)-one;

2-Carboxy-1-(3,4-methylenedioxyanilino)methyl-7-trifluoromethylimidazo[1,2-a]quinoxalin-4(5H)-one;

2-Ethoxycarbonyl-7-fluoro-1-methylimidazo[1,2-a]quinoxalin-4(5H)-one;

1-Carboxy-7-fluoro-2-methylimidazo[1,2-a]quinoxalin-4(5H)-one;

2-Ethoxycarbonyl-1-methyl-7-methylsulfonylimidazo[1,2-a]quinoxalin-4(5H)-one;

2-Carboxy-1-methyl-7-methylsulfonylimidazo[1,2-a]quinoxalin-4(5H)-one;

2-Carbamoyl-1-methyl-7-trifluoromethylimidazo[1,2-a]quinoxalin-4(5H)one;

2-Carbazoyl-1-(1-imidazolylmethyl)-7-trifluoromethylimidazo[1,2-a]quinoxalin-4(5H)-one;

1-(1-Imidazolylmethyl)-2-(2(3H)thioxo-1,3,4-oxadiazol-5-yl)-7-trifluoromethylimidazo[1,2-a]quinoxalin-4(5H)-one;

2-Hydroxymethyl-1-(1-imidazolylmethyl)-7-trifluoromethylimidazo[1,2-a]quinoxalin-4(5H)-one;

2-Formyl-1-(1-imidazolylmethyl)-7-trifluoromethylimidazo[1,2-a]quinoxalin-4(5H)-one;

2-Hydroxyiminomethyl-1-(1-imidazolylmethyl)-7-trifluoromethylimidazo[1,2-a]quinoxalin-4(5H)-one;

1-Benzylaminomethyl-2-ethoxycarbonyl-7-trifluoromethylimidazo[1,2-a]quinoxalin-4(5H)-one;

2-Benzylaminomethyl-2-carboxy-7-trifluoromethylimidazo[1,2-a]quinoxalin-4(5H)-one;

2-Ethoxycarbonyl-8-(1-imidazolyl)-1-methylimidazo[1,2-a]quinoxalin-4(5H)-one;

2-Carboxy-8-(1-imidazolyl)-1-methylimidazo[1,2-a]quinoxalin-4(5H)-one;

2-Ethoxycarbonyl-1-diethoxyphosphoryl-7-trifluoromethylimidazo[1,2-a]quinoxalin-4(5H)-one;

2-Ethoxycarbonyl-1-phosphonomethyl-7-trifluoromethylimidazo[1,2-a]quinoxalin-4(5H)-one;

2-Carboxy-1-phosphonomethyl-7-trifluoromethylimidazo[1,2-a]quinoxalin-4(5H)-one.

Other preferred compounds of the invention are:

1-(1-Imidazolylmethyl)-2-(2(3H)oxo-1,3,4-oxadiazol-5-yl)-7-trifluoromethylimidazo[1,2-a]quinoxalin-4(5H)-one;

1-(1-Imidazolylmethyl)-2-(2(3H)amino-1,3,4-oxadiazol-5-yl)-7-trifluoromethylimidazo[1,2-a]quinoxalin-4(5H)-one;

1-(1-Imidazolylmethyl)-2-(1H-tetrazol-5-yl)-7-trifluoromethylimidazo[1,2-a]quinoxalin-4(5H)-one;

2-Carboxy-8-(1-imidazolyl)-1-methyl-7-nitroimidazo[1,2-a]quinoxalin-4(5H)-one.

The invention also relates to a method of preparing the above mentioned compounds. The present compounds of formula I are prepared as illustrated in the following schemes:

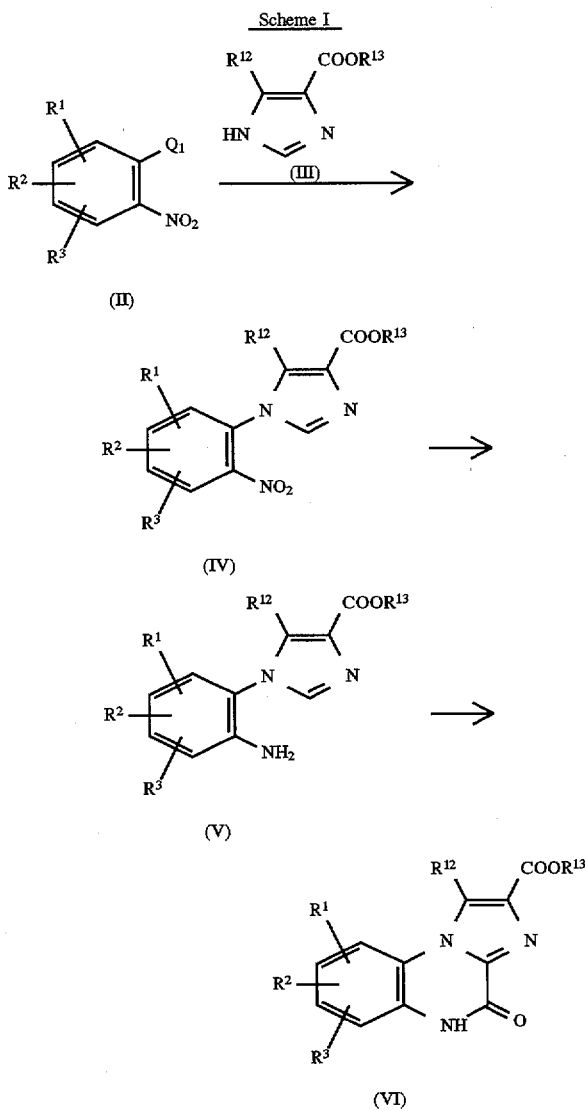

wherein $R^1$, $R^2$ and $R^3$ have the meanings defined above for formula I, $R^{12}$ is H or CH$_3$, $R^{13}$ is C$_{1-6}$-alkyl and $Q_1$ is halogen.

As illustrated in scheme I, treatment of an appropriately substituted ortho halo nitro aromatic (formula II) (prepared by standard methods known in the art) with a substituted imidazole (formula III) in an aprotic solvent (acetonitrile, dimethyl sulfoxide, dimethyl formamide or methylene chloride) at temperatures ranging from about 0° C. to about 150° C. gives the ortho imidazol-1-yl nitro aromatic (formula IV).

Reduction of the nitro group to an amino group is readily achieved by catalytic hydrogenation to form a compound of formula V. Cyclization to a compound of formula VI was proceeded by reacting a compound of formula V with 1 to 4 equivalent excess of a doubly activated carbonic acid derivative in an inert aprotic solvent at a temperature of from about 150° C. to about 200° C. for about 30 min. to 6 h. The doubly activated carbonic acid derivative is selected from 1-1'-carbonyldiimidazole, diphenyl carbonate phosgene or an equivalent, preferably carbonyldiimidazole. The aprotic solvent is selected from N-methylpyrrolidinone, tetralin, decalin, 1,2-dichlorobenzene, 1,3-dimethyl-2-imidazolidinone, preferably 1,2-dichlorobenzene. The temperature of the reaction is preferably 170°–180° C. with a reaction duration of about 1–4 h.

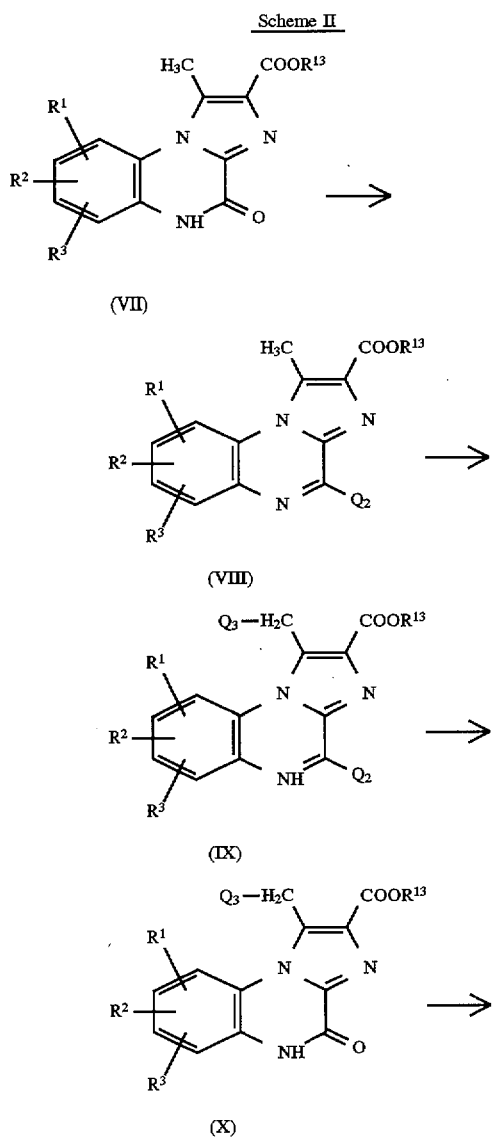

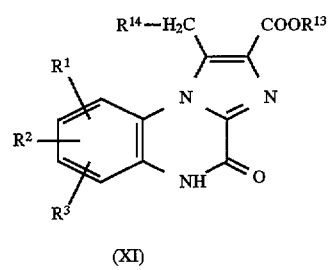

wherein $R^1$, $R^2$, $R^3$ have the meanings defined above in formula I and $R^{13}$ is $C_{1-6}$alkyl and $R^{14}$ is $POR'''R''''$, $NR^7R^8$ or a 5- or 6-membered nitrogen containing heterocyclic ring optionally substituted with one or two of phenyl, $C_{1-6}$-alkyl or halogen and $R'''$, $R''''$, $R^7$, $R^8$ have the meanings defined above for Formula I and $Q_2$, $Q_3$ are halogen.

Halogenation of a compound of formula VII to a compound of formula VIII may be effected by halogenating reagents such as phosgene, diphosgene, phosphorous pentachloride or thionyl chloride, preferably phosgene in dimethyl formamide at a temperature about 25°–50° C.

The second halogenation in the allylic position to a compound of formula IX is carried out with a N-halo amide such as for example N-bromosuccinimide and an initiator in a nonpolar anhydrous reagent such as boiling carbon tetrachloride or chloroform. The initiator is preferably 2,2'-azobis(2-methylproprionitrile).

Dehalogenation to the quinoxalinone (formula X) is preferably carried out in glacial acetic acid at elevated temperature.

Formation of a compound of formula XI wherein $R^{14}$ is $POR'''R''''$ is achieved by heating a compound of formula X in trialkyl phosphite. The hydrolysis is performed in two steps using at first bromotrimethyl silane followed by a reaction with hydrobromic acid.

Treatment of a compound of formula X with an appropriate amine to form a compound of formula Xi wherein $R^{14}$ is an amine may conveniently be effected in an organic solvent such as acetonitrile or acetone in some examples in the presence of a base for example potassium carbonate.

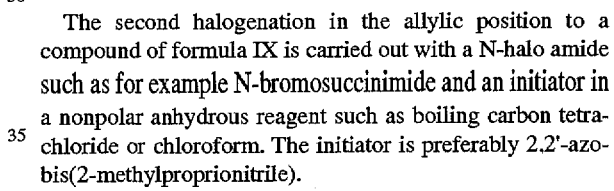

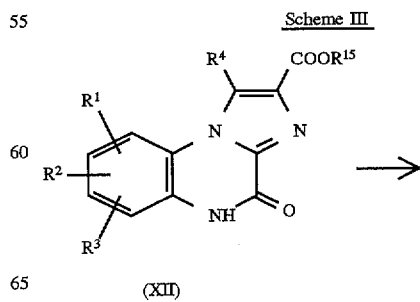

-continued
Scheme III

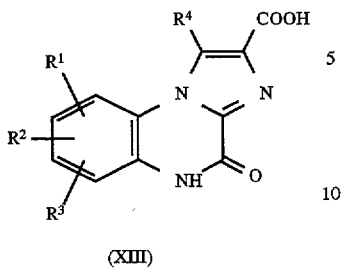

(XIII)

wherein

R¹, R², R³ and R⁴ have the meanings defined above for formula I and R¹⁵ is H or $C_{1-6}$-alkyl.

Hydrolysis of a compound of formula XII is performed by standard procedures either under basic or acidic conditions, preferably 2M potassium hydroxid or hydrobromic acid (48% in water).

Scheme IV

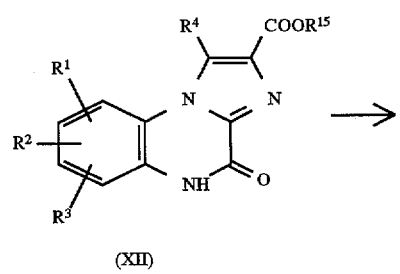

(XII)

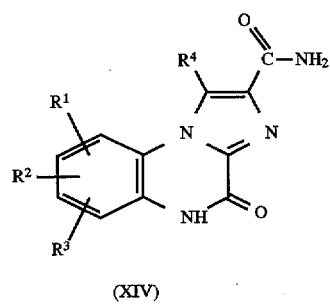

(XIV)

wherein

R¹, R², R³, R⁴ and R¹⁵ have the meanings defined above.

Standard methods are used to prepare the amide of formula XIV.

Scheme V

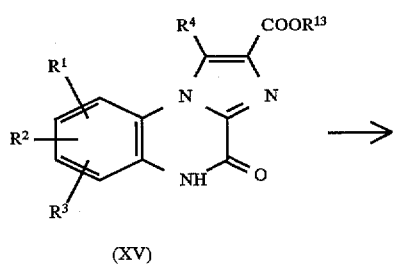

(XV)

-continued
Scheme V

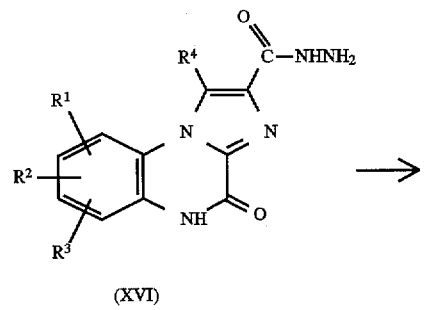

(XVI)

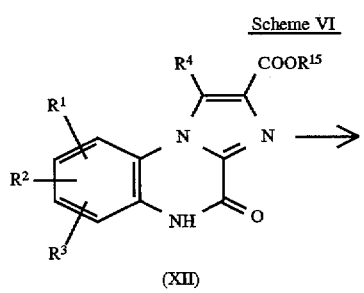

(XVII)

wherein

R¹, R², R³, R⁴, R¹³, X and Y have the meanings defined for formula I.

The hydrazides (formula XVI) are readily available by treating a compound of formula XV with hydrazine hydrate in a polar solvent as for example methanol. The 1,3,4-oxadiazole-2-thiones (formula XVII, wherein X=O, Y=S) is obtained by reaction of a compound of formula XVI with carbondisulfide under basic conditions.

A compound of formula XVI is converted to 1,3,4-oxadiazol-2-ones (formula XVII, wherein X=O, Y=O) by the addition of a doubly activated carbonic acid derivative such as 1,1'-carbonyldiimidazole in the presence of base. The 2-amino-1,3,4-oxadiazoles (formula XVII, wherein X=O, Y=NH) results from the action of cyanogen bromide and $Na_2CO_3$ on a compound of formula XVI.

Scheme VI

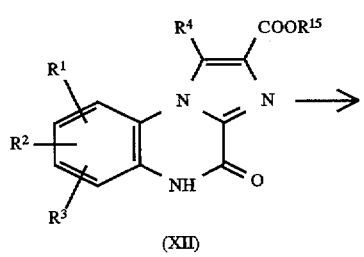

(XII)

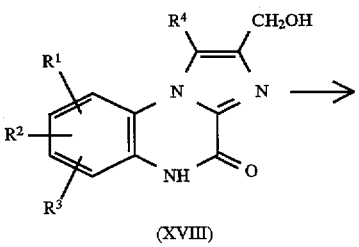

(XVIII)

-continued
Scheme VI

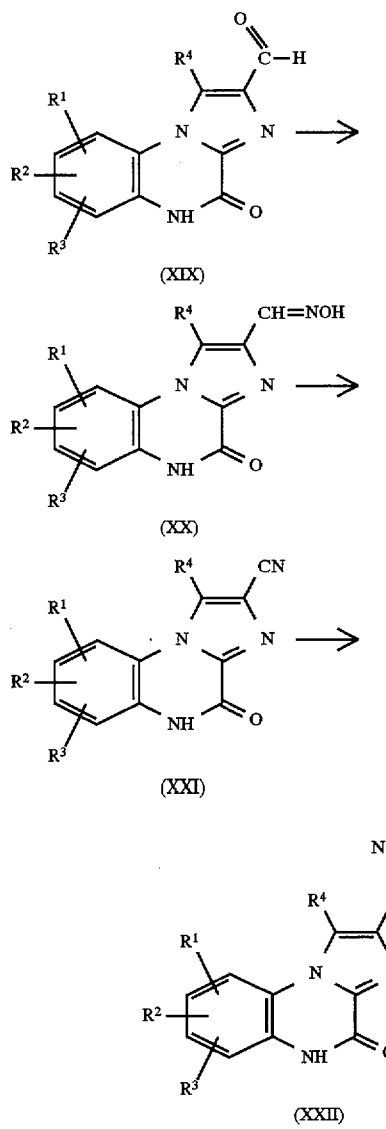

wherein
$R^1$, $R^2$, $R^3$, $R^4$ and $R^{15}$ have the meanings defined above for formula I.

Reduction of the carboxylic ester (formula XII) to the alcohol (formula XVIII) is achieved by standard procedure. The following oxidation to the aldehyde (formula XIX) can be performed with many oxidizing agents. To overcome solubility problems a Swern oxidation is preferred which is carried out in dichloromethane at −78° C., followed by a hydrolysis of a substituted 4-chloroimidazo[1,2-a]quinoxaline intermediate. The aldehyde (formula XIX) is converted to the oxime (formula XX) by reacting with hydroxylamine in a polar solvent as for example methanol. The aldoximes can be dehydrated to the nitriles (formula XXI) by a dehydrating agent. The cyclization to the tetrazoles (formula XXII) is preferably performed using sodiumazide and ammonium chloride in dimethylformamide.

The starting materials for which the preparation is not described herein are either known compounds or compounds which may be prepared in analogy with the preparation of known compounds or in analogy with known methods.

Modification in the benzene ring, which is not outlined in Scheme I to Scheme V is achieved at different reaction stages during the synthesis by standard methods known in the art.

The affinity of a substance for one or more of the different types of excitatory amino acid receptors may be studied in simple binding experiments. In essence, the method involves incubation of a particular selected radiolabelled ligand and the particular specific substance to be investigated with brain homogenate which contains the receptor. Measurement of receptor occupancy is made by determination of the radioactivity bound to the homogenate and subtraction of nonspecific binding.

AMPA receptor binding may be studied by using $^3$H-AMPA as radioligand.

The influence of glutamic acid analogues on secondary effects of glutamate receptor interactions may be studied in vitro by using the phenomenon of spreading depression in chicken retina. Such experiments will provide information as to the efficacies (agonist/antagonist) of the test substances. This is in contrast to binding studies, which only provide information on the affinities of the compounds for the receptor.

The pharmacological properties of the compounds of the present invention can be illustrated by determining their capability for displacing radioactively labelled 2-amino-3-hydroxy-5-methyl-4-isoxazolepropionic acid (AMPA) from the AMPA type receptors. The antagonistic properties of the compounds is demonstrated by their capability to antagonize quisqualic acid stimulated spreading depression in chicken retina.

The displacement activity of the compounds may be shown by determining the $IC_{50}$ value which represents the concentration (µM) which causes a displacement of 50% of the specific binding of $^3$H-AMPA.

The antagonism is measured by determining the $IC_{50}$ value which represents the concentration which produces a 50% maximal inhibition of quisqualic acid stimulated spreading depression in chicken retina.

$^3$H-AMPA binding (Test 1)

500/µl of thawed rat cerebral cortical membrane homogenate in Tris-HCl (30 mM), CaCl$_2$ (2.5 mM) and KSCN (100 mM) pH 7.1 were incubated at 0° C. for 30 min. with 25 µl $^3$H-AMPA (5 nM final concentration) and the test compound and buffer. Nonspecific binding was determined by incubation with L-glutamic acid (600/µM final concentration). The binding reaction was terminated by adding 5 ml of ice-cold buffer followed by filtration through Whatman GF/C glass fibre filters and 2×5 ml wash with ice-cold buffer. Bound radioactivity was measured by scintillation counting. IC$_{50}$ was determined by Hill analysis of at least four concentrations of test compound.

Spreading depression (Test 2)

Chicks (3–10 days old) were decapitated, the eyes enucleated and sectioned along the equatorial plane. After removal of the anterior chamber and the vitreous body, the posterior chamber of each eye was placed in a small petri dish containing a physiological saline solution (P.S.S.) of the following composition (mM) NaCl (100), KCl (6.0), CaCl$_2$ (1.0), MgSO$_4$ (1.0), NaHCO$_3$ (30), NaH$_2$PO$_4$ (1.0), glucose (20).

The solution was saturated with 100% O$_2$ and maintained at a temperature of 26° C.

The eyes were initially incubated in normal P.S.S. for 15–30 min. and then transferred to P.S.S. containing quisqualate (1 µg/ml). In this "stimulating solution" S.D.s start spontaneously usually from the edge of the retina, and can be easily observed by eye. The time taken for an S.D. to start in each eye was measured.

After a further 15 min. of incubation in normal P.S.S. the eyes were transferred to normal P.S.S. containing the test compound and incubated for 15 min. Thereafter the eyes were transferred to a "stimulating solution" containing the same concentration of the test compound. The time taken for an S.D. to start in each eye was measured again. The eyes were then placed back in normal P.S.S. and after 15 min. the time taken for S.D. to start was measured again, in order to assess the degree of recovery from any drug effects.

An increase in the time taken for S.D. to start of 30 seconds more than the control time is considered 100% inhibition of S.D. The drug effects therefore are expressed as the percentage maximum response obtained for a given dose. The test value can be quoted therefore as the concentration (µM) of test substance which produces a 50% maximal inhibition ($IC_{50}$).

Test results obtained by testing a compound of the present invention are shown in the following table 1.

TABLE I

|  | TEST 1 | TEST 2 |
| --- | --- | --- |
| Compound of example | $IC_{50}$ µM | $IC_{50}$ µM |
| example 2 | 0.45 | 1.1 |

The pharmaceutical preparations of compositions comprising the compounds of the invention may be administered to humans or animals by oral, rectal or parenteral route.

An effective amount of the active compound or a pharmaceutically acceptable salt thereof may be determined in accordance with the usual factors, such as the nature and severity of the condition and the weight of the mammal requiring treatment.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose, and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or colouring substances and the like, which do not deleteriously react with the active compounds.

Injectable solutions or suspensions, preferably aqueous solutions with the active compound dissolved in polyhydroxylated castor oil, are particularly suitable for parenteral administration.

Ampoules are convenient unit dosage forms.

Tablets, dragees, or capsules containing talc and/or a carrier or binder or the like are particularly suitable for oral administration. The carrier preferably is lactose and/or corn starch and/or potato starch.

A syrup, elixir, or the like can be used in the cases where a sweetened vehicle can be employed or is desired.

Generally, the compounds of this invention are dispensed in unit dosage form comprising 10–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains:

| Core: | | |
| --- | --- | --- |
| Active compound (as free compound or salt thereof) | | 100 mg |
| Colloidal silicon dioxide (Aerosil ®) | | 1.5 mg |
| Cellulose, microcryst. (Avicel ®) | | 70 mg |
| Modified cellulose gum (Ac-Di-Sol ®) | | 7.5 mg |
| Magnesium stearate | | 1 mg |
| Coating: | | |
| HPMC | approx. | 9 mg |
| *Mywacett ® 9-40T | approx. | 0.9 mg |

*Acylated monoglyceride used as plasticizer for film-coating

The free compounds of the present invention which form alkali metal or alkaline earth metal salts may be employed in such salt form. Such alkali metal or earth alkali metal salts are ordinarily formed by reacting the compound with an equivalent amount or excess of the selected alkali metal or earth alkali metal as the hydroxide, frequently and suitably by admixture in the presence of a neutral solvent, from which the salt may be precipitated or recovered in other conventional manner, e.g. by evaporation. Administration of a compound of the invention is often preferably in the form of a pharmaceutically acceptable water-soluble alkali metal or earth alkali metal salt thereof, and orally, rectally, or parenterally in the form of a pharmaceutical composition wherein it is present together with a pharmaceutically acceptable liquid or solid carrier or diluent.

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical composition and unit dosage forms thereof may comprise conventional ingredients in conventional proportions, with or without additional active compounds or principles, and such unit dosage forms may contain any suitable effective AMPA antagonistic amount of the active ingredient commensurate with the intended daily dosage range to be employed. Tablets containing 10 mg to 200 mg of active ingredient or, more specified 50 mg, per tablet, are accordingly suitable representative unit dosage forms.

Due to their high degree of AMPA antagonistic activity and their low toxicity, together presenting a most favourable therapeutic index, the compounds of the invention may be administered to a subject, e.g. a living animal body, in need of such treatment, elimination, alleviation, or amelioration of an indication which is sensitive to a change in the AMPA receptor condition, e.g. sclerosis, Parkinsonism, Alzheimer's disease, Huntington's disease, epilepsy, deficiencies seen after ischemia, anoxia, hypoglycemia, head and spinal cord trauma, psychosis, muscle rigidity, emesis and analgesia, often preferably in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Suitable dosage ranges are 10–200 milligrams daily, preferably 50–100 milligrams daily, and especially 70–100 milligrams daily, depending as usual upon the exact mode of administration, form in which administered, the indication towards which the administration is directed, the subject involved and the body weight of the subject involved, and the preference and experience of the physician or veterinarian in charge.

Such method of treating may be described as the treatment of an indication caused by or related to hyperactivity of the excitatory neurotransmitters, and particularly the AMPA receptors in a subject in need thereof, which comprises the step of administering to the said subject a neurologically effective amount of an AMPA antagonistic compound of the invention, or a pharmaceutically acceptable salt thereof.

Furthermore, the present invention relates to the use of a compound of the invention for preparing a medicament for treating an indication caused by or related to hyperactivity of the excitatory neurotransmitters, and particularly the AMPA receptors in a subject in need thereof.

The invention will now be described in further detail with reference to the following examples:

EXAMPLE 1

2-Ethoxycarbonyl-1-methyl-7-trifluoromethylimidazo[1,2-a]quinoxalin 4(5H)-one

Step a. 4-Ethoxycarbonyl-5-methyl-1-(2-nitro-4-trifluoromethylphenyl)-1H-imidazole A mixture of 4-fluoro-3-nitrobenzotrifluoride (20.5 ml, 146.5 mmol), ethyl 4-methyl-5-imidazolecarboxylate (23 g, 149.0 mmol), potassium carbonate (20.5 g, 148.5 mmol) and acetonitrile (200 ml) was stirred at 70° C. for 16 h. The solvent was removed under reduced pressure, and the residue submitted to flash chromatography on silica gel 60 eluting with toluene graduated to toluene/ethyl acetate (1:19) to give 42 g (84%) of 4-ethoxycarbonyl-5-methyl-1-(2-nitro-5-trifluoromethylphenyl)-1H-imidazole. M.p. 139.5°–140.5° C.

$^1$H NMR (CDCl$_3$): δ1.45 (t, 3H), 2.35 (s, 3H), 4.40 (q, 2H), 7.50 (s, 1H), 7.65 (d, 1H), 8.10 (dd, 1H), 8.45 (d, 1H).

Step b. 1-(2-Amino-4-trifluoromethylphenyl)-4-ethoxycarbonyl-5-methyl-1H-imidazole A solution of 4-ethoxycarbonyl-5-methyl-1-(2-nitro-5-trifluoromethylphenyl)-1H-imidazole (17.0 g, 49.5 mmol) in ethanol (500 ml) was hydrogenated in a PARR hydrogenation apparatus at 30 psi and 25° C. using 1.0 g 5% Pd-C as a catalyst. The reaction mixture was filtered and concentrated in vacuo. Recrystallization from ethyl acetate/petroleum ether gave 12.3 g (79%) of 1-(2-amino-4-trifluoromethylphenyl)-4-ethoxycarbonyl-5-methyl-1H-imidazole. M.p. 185°–186° C.

$^1$H NMR (CDCl$_3$): δ1.40 (t, 3H), 2.40 (s, 3H), 4.10 (bs, 1H), 4.40 (q, 2H), 7.00–7.20 (m, 3H), 7.45 (s, 1H).

Step c. 2-Ethoxycarbonyl-1-methyl-7-trifluoromethylimidazo[1,2-a]quinoxalin-4(5H)-one A mixture of 1-(2-amino-4-trifluoromethylphenyl)-4-ethoxycarbonyl-5-methyl-1H-imidazole (12.3 g, 39.3 mmol), 1,1'-carbonyldiimidazole (7.0 g, 43.2 mmol) in 1,2-dichlorobenzene (250 ml) was stirred at 180° C. for 6 h under N$_2$. The reaction mixture was cooled to room temperature. The precipitate was filtered off and washed with acetone to give 10.2 g (77%) of the title compound. M.p. >250° C.

$^1$H NMR (DMSO-d$_6$): δ1.35 (t, 3H), 3.15 (s, 3H), 4.30 (q, 2H), 7.6 (d, 1H), 7.65 (s, 1H), 8.40 (d, 1H).

EXAMPLE 2

2-Carboxy-1-methyl-7-trifluoromethylimidazo[1,2-a]quinoxalin-4(5H)-one

A suspension of 2-ethoxycarbonyl-1-methyl-7-trifluoromethylimidazo [1,2-a]quinoxalin-4(5H)-one (960 mg, 2.8 mmol) in 2M potassium hydroxide (30 ml) was stirred at 80° C. for 4 h. The reaction mixture was added water (25 ml) and pH adjusted to pH 7 with 1N hydrochloride acid. The precipitate was filtered off and washed with water. Recrystallization from glacial acetic acid afforded 650 mg (74%) of the title compound as the acetate. M.p. >250° C.

$^1$H NMR (DMSO-d$_6$): δ1.90 (s, 3H), 3.15 (s, 3H), 7.60 (d, 1H), 7.70 (s, 1H), 8.40 (d, 1H), 12.10 (bs, 1H), 12.5 (bs, 1H).

EXAMPLE 3

1-Bromomethyl-2-ethoxycarbonyl-7-trifluoromethylimidazo[1,2-a]quinoxalin-4(5H)-one Step a. 4-Chloro-2-ethoxycarbonyl-1-methyl-7-trifluoromethylimidazo[1,2-a]quinoxaline To a suspension of 2-ethoxycarbonyl-1-methyl-7-trifluoromethylimidazo[1,2-a]quinoxalin-4(5H)-one (Example 1) (88 g, 259 mmol) in DMF (1.5 l) was dropwise added a solution of 28% phosgene in toluene (0.5 l, 960 mmol). The mixture was stirred at 50° C. for 1 h and overnight at 25° C. followed by evaporation in vacuo. The residue was stirred with ice-cooled water. The solid was collected by filtration and washed with water to yield 83,4 g (95%) of 4-chloro-2-ethoxycarbonyl-1-methyl-7trifluoromethylimidazo[1,2-a]quinoxaline. M.p. 182°–183° C.

$^1$H NMR (CDCl$_3$): δ1.50 (t, 3H), 3.35 (s, 3H), 4.50 (q, 2H), 7.90 (dd, 1H), 8.35 (d, 1H), 8.50 (d, 1H).

Step b. 1-Bromomethyl-4-chloro-2-ethoxycarbonyl-7-trifluoromethylimidazo[1,2-a]quinoxaline A mixture of 4-chloro-2-ethoxycarbonyl-1-methyl-7-trifluoromethylimidazo[1,2-a]quinoxaline (830 g, 232 mmol), N-bromosuccinimide (68,0 g, 382 mmol) and 2.2'-azobis(2-methylpropionitrile)(200 mg, 1.2 mmol) in tetrachloromethane (1.5 l) was heated at reflux for 18 h, allowed to cool and the product collected by filtration. The product was dissolved in dichloromethane (2 l) and washed with water, dried (MgSO$_4$), followed by purification with silica gel 60 (1 g). The organic phase was filtered and evaporated in vacuo. The residue was suspended in petroleum ether to yield 91.7 g (91%) of 1-bromomethyl-4-chloro-2-ethoxycarbonyl-7-trifluoromethyl-imidazo[1,2-a]quinoxaline which was collected by filtration. M.p. 196°–198° C.

$^1$H NMR (CDCl$_3$): δ1.50 (t, 3H), 4.60 (q, 2H), 5.60 (s, 2H), 6.05 (dd, 1H), 8.45 (d, 1H), 8.60 (d, 1H).

Step c. 1-Bromomethyl-2-ethoxycarbonyl-7-trifluoromethylimidazo[1,2-a]quinoxalin-4(5H)-one A suspension of 1-bromomethyl-4-chloro-2-ethoxycarbonyl-7-trifluoromethylimidazo[1,2-a] quinoxaline (91.0 g, 208 mmol) in glacial acetic acid (750 ml) was heated at 130° C. for 2.5 h. The solvent was removed under reduced pressure and the residue was stirred with ice-cooled water to give 81.2 g (93%) of the title compound. M.p. 247°–248° C.

$^1$H NMR (CDCl$_3$): δ1.50 (t, 3H), 4.55 (q, 2H), 5.50 (s, 2H), 7.70 (d, 1H), 7.85 (s, 1H), 8.40 (d, 1H), 12.05 (bs, 1H).

EXAMPLE 4

1-Bromomethyl-2-carboxy-7-trifluoromethylimidazo [1,2-a]quinoxalin-4(5H)-one

A suspension of 1-bromomethyl-2-ethoxycarbonyl-7-trifluoromethylimidazo[1,2-a]quinoxalin-4-(5H)-one (Example 3) (500 mg, 1.2 mmol) in hydrobromic acid (48% in water) (25 ml) was stirred at 80° C. for 16 h. The mixture was concentrated in vacuo, and the residue stirred with water to give 340 mg (73%) of the title compound, which was isolated by filtration. M.p. >250° C.

$^1$H NMR (DMSO-d$_6$): δ5.70 (s, 2H), 7.70 (d, 1H), 7.75 (s, 1H), 8.45 (d, 1H), 12.35 (s, 1H).

EXAMPLE 5

2-Ethoxycarbonyl-1-(1-imidazolylmethyl)-7-trifluoromethylimidazo[1,2-a]quinoxalin-4(5H)-one A suspension of 1-bromomethyl-2-ethoxycarbonyl-7-trifluoromethylimidazo[1,2-a]quinoxalin-4(5H)-one (Example 3) (4.18 g, 10.0 mmol) and imidazole (1.5 g, 22.0 mmol) in acetonitrile (200 ml) was stirred at 80° C. for 2 h and overnight at 25° C. The solvent was evaporated in vacuo and the residue submitted to flash chromatography on silica gel 60 eluting with dichloromethane/methanol (19:1) graduated to dichloromethane/methanol (1:9). The purified product was washed with water to give 2.0 g (49%) of the title compound. M.p. 187°–189° C.

$^1$H NMR (MeOD): δ1.40 (t, 3H), 4.40 (q, 2H), 6.25 (s, 2H), 7.00 (s, 1H), 7.20 (s, 1H), 7.50 (dd, 1H), 7.70 (d, 1H,), 7.85 (s, 1H), 7.95 (d, 1H).

EXAMPLE 6

2-Carboxy-1-(1-imidazolylmethyl)-7-trifluoromethylimidazo[1,2-a]quinoxalin-4(5H)-one A suspension of 2-ethoxycarbonyl-1-(1-imidazolylmethyl)-7-trifluoromethylimidazo[1,2-a]quinoxalin-4(5H)-one (Example 5) (1.9 g, 4.69 mmol) in hydrobromic acid (48% in water) (100 ml) was stirred at 80° C. for 16 h. The mixture was concentrated in vacuo, and the residue stirred with methanol to give 1.95 g (88%) of the title compound as a HBr salt, which was isolated by filtration.

$^1$H NMR (DMSO-d$_6$): δ6.40 (s, 2H), 7.45 (dd, 1H), 7.75 (s, 2H), 7.80 (d, 1H), 7.95 (d, 1H), 9.10 (s, 1H), 12.40 (s, 1H).

EXAMPLE 7

2-Ethoxycarbonyl-1-(2-methyl-1-imidazolyl)methyl-7-trifluoromethylimidazo[1,2-a]quinoxalin-4(5H)-one A suspension of 1-bromomethyl-2-ethoxycarbonyl-7-trifluoromethylimidazo[1,2-a]quinoxalin-4(5H)-one (Example 3) (4.18 g, 10.0 mmol) and 2-methylimidazole (1.8 g, 22.0 mmol) in acetonitrile (200 ml) was stirred at 80° C. for 4 h. The solvent was evaporated in vacuo and the residue submitted to flash chromatography on silica gel 60 eluting with dichloromethane/methanol (19:1). The purified product was washed with water to give 2.6 g (62%) of the title compound. M.p. >250° C.

$^1$H NMR (MeOD): δ1.35 (t, 3H), 2.65 (s, 3H), 4.40 (q, 2H), 6.10 (s, 2H), 6.70 (d, 1H), 6.75 (d, 1H), 7.50 (m, 1H), 7.70–7.75 (m, 2H).

EXAMPLE 8

2-Carboxy-1-(2-methyl-1-imidazolyl)methyl-7-trifluoromethylimidazo [1,2-a]quinoxalin-4(5H)-one A suspension of 2-ethoxycarbonyl-1-(2-methyl-1-imidazolyl)methyl-7-trifluoromethylimidazo[1,2-a] quinoxalin-4(5H)-one (Example 7) (300 mg, 0.72 mmol) in hydrobromic acid (48% in water) (20 ml) was stirred at 80° C. for 16 h. The precipitate was collected and washed with ether. M.p. >250° C.

$^1$H NMR (MeOD+DMSO-d$_6$): δ2.90 (s, 3H), 6.35 (s, 2H), 7.30 (d, 1H), 7.40 (d, 1H), 7.60 (dd, 1H), 7.75 (d, 1H), 8.05 (d, 1H).

EXAMPLE 9

1-(4,5-Dichloro-1-imidazolyl)methyl-2-ethoxycarbonyl-7-trifluoromethylimidazo[1,2-a]quinoxalin-4(5H)-one A suspension of 1-bromomethyl-2-ethoxycarbonyl-7-trifluoromethylimidazo[1,2-a]quinoxalin-4(5H)-one (Example 3) (2.1 g, 5.0 mmol), 4,5-dichloroimidazole (1.5 g, 11.0 mmol) and potassium carbonate (1.5 g, 11 mmol) in acetonitril (100 ml) was stirred at 80° C. for 5 h and overnight at room temperature. The solvent was evaporated in vacuo and the residue submitted to flash chromatography on silica gel 60 eluting with dichloromethane/methanole (19:1) to give 540 mg (23%) of the title compound. M.p. 240° C.

$^1$H-NMR (MeOD+DMSO): δ1.35 (t, 3H), 4.40 (q, 2H), 6.10 (s, 2H), 7.55 (s, 1H), 7.50–7.60 (dd, 1H), 7.75–7.85 (m, 2H).

EXAMPLE 10

2-Carboxy-1-(4,5-dichloro-1-imidazolyl)methyl-7-trifluoromethylimidazo[1,2-a]quinoxalin-4(5H)-one A suspendion of 1-(4,5-dichloro-1-imidazolyl)methyl-2-ethoxycarbonyl-7trifluoromethylimidazo[1,2-a]quinoxalin-4(5H)-one (Example 9) (120 mg, 0.25 mmol) in hydrobromic acid (48% in water) (10 ml) was stirred at 80° C. for 6 h. The mixture was concentrated in vacuo and the residue added acetone. The title compound was isolated by filtration to yield 80 mg (61%) as a hydrobromic salt. M.p. 213°–215° C.

$^1$H-NMR (DMSO-d$_6$): δ6.05 (s, 2H), 7.52 (s, 1H), 7.55 (d, 1H), 7.75 (s, 1H), 7.85 (d, 1H).

EXAMPLE 11

2-Ethoxycarbonyl-1-(4-methyl-1-piperazinyl)methyl-7-trifluoromethylimidazo[1,2-a]quinoxalin-4 (5H)-one To a solution of 1-bromomethyl-2-ethoxycarbonyl-7-trifluoromethylimidazo[1,2-a]quinoxalin-4(5H)-one (Example 3) (630 mg, 1.5 mmol) in acetonitrile (180 ml) was added N-methylpiperazine (200 mg, 2.0 mmol). Stirring of the mixture was continued overnight at 25° C. followed by evaporation in vacuo. The residue was submitted to flash chromatography on silica gel 60 eluting with dichloromethane/methanol/ammonium hydroxide (90:10:0.5) to give 450 mg (69%) of the title compound. M.p. 255° C.

$^1$H NMR (MeOD): δ1.40 (t, 3H), 2.30 (s, 3H), 2.55 (bs, 2H), 2.75 (bs, 2H), 4.35–4.50 (m, 4H), 7.60–7.70 (m, 2H), 8.75 (d, 1H).

EXAMPLE 12

2-Carboxy-I -(4-methyl-1-piperazinyl)methyl-7-trifluoromethylimidazo[1,2-a]quinoxalin-4(5H)-one A solution of 2-ethoxycarbonyl-1-(4-methyl-1-piperazinyl)methyl-7-trifluoromethylimidazo[1,2-a]

quinoxalin-4(5H)-one (Example 11) (380 mg, 0.87 mmol) in hydrobromic acid (48% in water) (20 ml) was stirred at 80° C. for 30 h. The mixture was concentrated in vacuo and the residue stirred with ether. The product which was isolated by filtration was recrystallized from methanol/ether to afford 260 mg (57%) of the title compound as a HBr salt. M.p. >240° C.

$^1$H NMR (DMSO-d$_6$): δ2.60 (m, 2H), 2.80 (d, 3H), 2.95 (m, 2H), 3.10 (m, 2H), 3.40 (m, 2H), 4.40 (s, 2H), 7.70 (m, 2H), 8.45 (d, 1H), 9.50 (bs, 1H), 12.20 (s, 1H).

EXAMPLE 13

2-Ethoxycarbonyl-1-(3,4-methylenedioxyanilino)methyl-7-trifluoromethylimidazo[1,2-a]quinoxalin-4(5H)-one A mixture of 1-bromomethyl-2-ethoxycarbonyl-7-trifluoromethylimidazo[1,2-a]quinoxalin-4(5H)-one (Example 3) (2.1 g, 5.0 mmol) and 3,4-methylenedioxyaniline (1.5 g, 11 mmol) in acetonitrile (100 ml) was stirred at 80° C. for 3 h and overnight at 25° C. The solvent was evaporated in vacuo and the residue submitted to flash chromatography on silica gel 60 eluting with dichloromethane/methanol (19:1). The purified product was washed with acetone to afford 1.55 g (65%) of the title compound. M.p. >250° C.

$^1$H NMR (MeOD+DMSO-d$_6$): δ1.35 (t, 3H), 4.35 (q, 2H), 4.95 (s, 2H), 5.90 (s, 2H), 6.25 (dd, 1H), 6.45 (d, 1H), 6.75 (d, 1H), 7.55 (dd, 1H), 7.75 (d, 1H), 8.25 (d, 1H).

EXAMPLE 14

2-Carboxy-1-(3,4-methylenedioxyanilino)methyl-7-trifluoromethylimidazo[1,2-a]quinoxalin-4(5H)-one A suspension of 2-ethoxycarbonyl-1-(3,4-methylenedioxyanilino)methyl-7-trifluoromethylimidazo[1,2-a]quinoxalin-4(5H)-one (Example 13) (500 mg, 1.1 mmol) in 2M potassium hydroxide (50 ml) and methanol (50 ml) was stirred at 60° C. for 4 h. The reaction mixture was concentrated to half volume and the precipitate isolated by filtration to give 375 mg (74%) of the title compound as the potassium slat. M.p. >250° C.

$^1$H NMR (DMSO-d$_6$+TFA): δ5.05 (s, 2H), 5.85 (s, 2H), 6.35 (m, 1H), 6.55 (s, 1H), 6.75 (m, 1H), 7.50 (d, 1H), 7.70 (s, 1H), 8.20 (d, 1H).

EXAMPLE 15

2-Ethoxycarbonyl-7-fluoro-1-methylimidazo[1,2-a]quinoxalin-4(5H)-one

The title compound was prepared from 2,5-difluoronitrobenzene following the procedure outlined in Example 1. M.p. >250° C.

$^1$H NMR (DMSO-d$_6$): δ1.35 (t, 3H), 4.35 (q, 2H), 7.15 (m, 2H), 8.25 (m, 1H).

EXAMPLE 16

2-Carboxy-7-fluoro-1-methylimidazo[1,2-a]quinoxalin-4(5H)-one

The title compound was prepared from 2-ethoxycarbonyl-7-fluoro-1-methylimidazo[1,2-a]quinoxalin-4(5H)-one following the procedure outlined in Example 2. M.p. >250° C.

$^1$H-NMR (DMSO-d$_6$): δ3.10 (s, 3H), 7.15 (m, 2H), 8.25 (m, 1H), 12.00 (s, 1H), 12.90 (bs, 1H).

EXAMPLE 17

2-Ethoxycarbonyl-1-methyl-7-methylsulfonylimidazo[1,2-a]quinoxalin-4(5H)-one

The title compound was prepared from 4-fluoro-3-nitrophenylmethylsulfone following the procedure outlined in Example 1. M.p. >250° C.

Ms (70 eV): m/z 349 (20%, M$^+$), 323 (56), 303 (21), 277 (44), 262 (20), 249 (77), 224 (39), 197 (100), 118 (48), 79 (80), 63 (85).

EXAMPLE 18

2-Carboxy-1-methyl-7-methylsulfonylimidazo[1,2-a]quinoxalin-4(5H)-one

A suspension of 2-ethoxycarbonyl-1-methyl-7-methylsulfonylimidazo[1,2-a]quinoxalin-4(5H)-one (430 mg, 1.23 mmol) in 2M potassium hydroxide (15 ml) was stirred at 80° C. for 6 h. The reaction mixture was added water (10 ml) and pH adjusted to pH 7 with 1N hydrochloride acid. The precipitate was filtered off and washed with water to give 100 mg (25%) of the title compound as the potassium salt. M.p. 228° C.

$^1$H NMR (TFA): δ2.65 (s, 3H), 3.50 (s, 3H), 7.90 (d, 1H), 8.25 (dd, 1H), 8.75 (bs, 1H), 9.25 (s, 1H).

EXAMPLE 19

2-Carbamoyl-1-methyl-7-trifluoromethylimidazo[1,2-a]quinoxalin-4(5H)-one

To a suspension of 2-carboxy-1-methyl-7-trifluoromethylimidazo[1,2-a]quinoxalin-4(5H)-one (Example 2) (85 mg, 0.25 mmol) in dry toluene (20 ml) was added thionyl chloride (0.5 ml). The reaction mixture was stirred at reflux for 40 min. and at room temperature overnight. The mixture was concentrated in vacuo, and the residue added ice cooled ammonium hydroxide 25% in water (5 ml). After 2 h at 25° C. the title compound was collected by filtration and washed with water to give 60 mg (77%). M.p. >250° C.

$^1$H NMR (DMSO-d$_6$): δ3.20 (s, 3H), 7.40 (s, 1H), 7.60 (d, 1H), 7.70 (s, 1H), 7.72 (s, 1H), 8.40 (d, 1H), 1.95 (bs, 1H).

EXAMPLE 20

2-Carbazoyl-1-(1-imidazolylmethyl)-7-trifluoromethylimidazo[1,2-a]quinoxalin-4(5H)-one A solution of 2-ethoxycarbonyl-1-(1-imidazolylmethyl)-7-trifluoromethylimidazo[1,2-a]quinoxalin-4(5H)-one (Example 5) (1.0 g, 2.5 mmol) in methanol (50 ml) was added hydrazine hydrate (500 μl, 10.3 mmol) in methanol (20 ml). The reaction mixture was stirred at 60° C. for 16 h and then concentrated in vacuo. The residue was added ether and the solid isolated by filtration to yield 860 mg (88%) of the title compound. M.p. >250° C.

$^1$H NMR (DMSO-d$_6$); δ5.90 (bs), 6.30 (s, 2H), 6.90 (s, 1H), 7.15 (s, 1H), 7.40 (d, 1H), 7.70 (s, 1H), 7.75 (s, 1H), 7.90 (d, 1H).

EXAMPLE 21

1-(1-Imidazolylmethyl)-2-(2(3H)thioxo-1,3,4-oxadiazol-5-yl)-7-trifluoromethylimidazo[1,2-a]quinoxalin-4(5H)-one 2-Carbazoyl-1-(1-imidazolylmethyl)-7-trifluoromethylimidazo[1,2-a]quinoxalin-4(5H)-one (Example 20) (390 mg, 1.0 mmol) in methanol (6 ml) was cooled to 0° C. Carbon disulphide (150 μl, 2.5 mmol) was added, followed by potassium hydroxide (75 mg, 1.1 mmol). The solution was heated at reflux for 7 h and allowed to cool to room temperature overnight. The precipitate was isolated by filtration and washed with methanol to yield 140 mg (30%) of the title compound as the potassium salt. M.p. >250° C.

$^1$H NMR (DMSO): δ6.25 (s, 2H), 6.85 (s, 1H), 7.15 (s, 1H), 7.45 (d, 1H), 7.70 (s, 1H), 7.75 (s, 1H), 7.90 (d, 1H), 12.25 (bs, 1H).

EXAMPLE 22

2-Hydroxymethyl-1-(1-imidazolylmethyl)-7-trifluoromethylimidazo[1,2-a]quinoxalin-4(5H)-one To a suspension of lithium aluminium hydride (400 mg, 10.5 mmol) in dry tetrahydrofuran (200 ml) was added 2-ethoxycarbonyl-1-(1-imidazolylmethyl)-7-trifluoromethylimidazo[1,2-a]quinoxalin-4(5H)-one (3.6 g, 8.8 mmol) in small portions. After 20 min. at 25° C. the temperature was raised to reflux for 2 h. The reaction mixture was cooled to room temperature, quenched with water and then filtered. The solvent was evaporated in vacuo and the residue dissolved in 20% sulphuric acid. The precipitate was filtered off and the liquid phase added potassium hydroxide to pH 11. The product was isolated by continuous liquid/liquid extraction (ethyl acetate) overnight to give 2.1 g (67%) of the title compound. M.p. 215° C.

$^1$H NMR (MeOD): δ4.85 (s, 2H), 6.00 (s, 2H), 7.00 (s, 1H), 7.20 (s, 1H), 7.45 (dd, 1H), 7.65 (d, 1H), 7.80 (s, 1H), 7.85 (d, 1H).

EXAMPLE 23

2-Formyl-1-(1-imidazolylmethyl)-7-trifluoromethylimidazo[1,2-a]quinoxalin-4(5H)-one A mixture of dichloromethane (30 ml) and oxalyl chloride (1.5 ml, 16.5 mmol) is under stirring at −50° C. to −60° C. added dimethyl sulfoxide (2.8 ml, 36 mmol) diluted with dichloromethane (15 ml). The reaction mixture is stirred for 2 min. followed by addition within 10 min. of 2-hydroxymethyl-1-(1-imidazolylmethyl)-7-trifluoromethylimidazo[1,2-a]quinoxalin-4(5H)-one (Example 22) (1.65 g, 4.5 mmol) in dichloromethane (5 ml) and dimethylsulfoxide (10 ml). The stirring was continued for an additional 15 min. Triethylamine (12 ml, 86 mmol) was added and the reaction mixture was stirred for 5 min. and then allowed to warm up to room temperature. Water (300 ml) was added and the aqueous layer was reextracted with additional dichloromethane (4×100 ml). The organic layers were combined, washed with saturated sodium chloride solution (250 ml) and dried with anhydrous magnesium sulphate. The filtered solution was concentrated in vacuo to give crude 4-chloro-2-formyl-1-(1-imidazolylmethyl)-7-trifluoromethylimidazo[1,2-a]quinoxaline which was hydrolysed to the title compound in 10 min at 40° C. with glacial acetic acid (30 min.). The mixture was concentrated in vacuo and the residue diluted in water. Saturated sodium hydrogen carbonate was added and the aldehyde extracted with acetonitrile (6×250 ml) to give 830 mg (50%) of the title compound. M.p. >250° C.

$^1$H NMR (DMSO-d$_6$): δ6.20 (s, 2H), 6.90 (s, 1H), 7.20 (s, 1H), 7.55 (d, 1H), 7.70 (s, 1H), 7.75 (s, 1H), 7.95 (d, 1H), 10.15 (s, 1H), 12.35 (s, 1H).

EXAMPLE 24

2-Hydroxyiminomethyl-1-(1-imidazolylmethyl)-7-trifluoromethylimidazo[1,2-a]quinoxalin-4(5H)-one To a solution of 2-formyl-1-(1-imidazolylmethyl)-7-trifluoromethylimidazo[1,2-a]quinoxalin-4(5H)-one (250 mg, 0.69 mmol) in methanol (10 ml) was added a mixture of hydroxylammonium chloride (65 mg, 0.95 mmol) and sodiumacetate (150 mg, 1.10 mmol) in methanol (10 ml). The reaction mixture was heated at 70° C. for 1.5 h, followed by addition of water (10 ml). The precipitate was filtered off and washed with water. Recrystalization from isopropanol/petroleum ether gave 150 mg (58%) of the title compound. M.p. 227.5°–228° C.

$^1$H-NMR (DMSO-d$_6$): δ6.05 (s, 2H), 6.90 (s, 1H), 7.15 (s, 1H), 7.50 (d, 1H), 7.70 (m, 2H), 7.85 (d, 1H), 8.35 (s, 1H), 11.65 (s, 1H), 12.25 (s, 1H).

EXAMPLE 25

1-Benzylaminomethyl-2-ethoxycarbonyl-7-trifluoromethylimidazo[1,2-a]quinoxalin-4(5H)-one The title compound was prepared from 1-bromomethyl-2-ethoxycarbonyl-7-trifluoromethylimidazo[1,2-a]quinoxalin-4(5H)-one (Example 3) following the procedure outlined in Example 9. M.p. >250° C.

EXAMPLE 26

1-Benzylaminomethyl-2-carboxy-7-trifluoromethylimidazo[1,2-a]quinoxalin-4(5H)-one The title compound was prepared from 1-benzylaminomethyl-2-ethoxycarbonyl-7-trifluoromethylimidazo[1,2-a]quinoxalin-4(5H)-one (Example 25) following the procedure outlined in Example 4. M.p. 248°–248.5° C.

$^1$H-NMR (DMSO-d$_6$): δ4.95 (s, 2H), 4.60 (s, 2H), 7.25–7.40 (m, 5H), 7.50 (d, 1H), 7.70 (s, 1H), 8.45 (d, 1H), 12.15 (s, 1H).

EXAMPLE 27

2-Ethoxycarbonyl-8-(1-imidazolyl)-I-methylimidazo[1,2-a]quinoxalin-4(5H)-one

Step a. 4-Ethoxycarbonyl-5-methyl-1-(2-nitro-5-fluorophenyl)-1H-imidazole

A mixture of 2,4-difluoronitrobenzene (36.6 g, 230 mmol), ethyl 4-methyl-5-imidazolecarboxylate (35.6 g, 231 mmol), potassium carbonate (36.5 g, 264.4 mmol) and acetonitrile (250 ml) was stirred at 25° C. for 96 h. The reaction mixture was filtered and the solvent removed under reduced pressure. The residue was submitted to flash chromatography on silica gel 60 eluting with toluene graduated to toluene/ethyl acetate (1:1) to give 30.5 g (65%) of 4-ethoxycarbonyl-5-methyl-1-(2-nitro-5-fluorophenyl)-1H-imidazole.

$^1$H-NMR (CDCl$_3$): δ1.40 (t, 3H), 2.35 (s, 3H), 4.40 (q, 2H), 7.70 (dd, 1H), 7.40–7.50 (m, 1H), 7.50 (s, 1H), 8.25 (dd, 1H).

Step b. 4-Ethoxycarbonyl-5-methyl-1-(2-nitro-5-(1-imidazolyl)phenyl)-1H-imidazole A mixture of 4-ethoxycarbonyl-5-methyl-1-(2-nitro-5-fluorophenyl)-1H-imidazole (20.0 g, 68 mmol), imidazole (4.7 g, 69 mmol), potassium carbonate (9.5 g, 69 mmol) and acetonitrile (150 ml) was stirred at 80° C. for 16 h. The solvent was removed under reduced pressure and the residue dissolved in ethyl acetate and washed twice with water. The organic phase was dried (MgSO$_4$), filtered and evaporated in vacuo to give 14.1 g (61%) of 4-ethoxycarbonyl-5-methyl-1-(2-nitro-5-(1-imidazolyl) phenyl)-1H-imidazole.

$^1$H-NMR (CDCl$_3$): δ1.40 (t, 3H), 2.40 (s, 3H), 4.40 (q, 2H), 7.30 (s, 1H), 7.45–7.55 (m, 2H), 7.65 (d, 1H), 7.80 (dd, 1H), 8.10 (s, 1H), 8.35 (d, 1H).

Step c. 1-(2-Amino-5-(1-imidazolyl)phenyl)-4-ethoxycarbonyl-5-methyl-1H-imidazole A solution of 4-ethoxycarbonyl-5-methyl-1-(2-nitro-5-(1-imidazolyl)phenyl)-1H-imidazole (14 g, 41 mmol) in ethanol (1.0 l) was hydrogenated in a PARR hydrogenation apparatus at 30 psi and 25° C. using 1.0 g 5% Pd-C as a catalyst. The reaction mixture was filtered and concentrated in vacuo to give 12.4 g (98%) of 1-(2-amino-5-(1-imidazolyl)phenyl)-4-ethoxycarbonyl-5-methyl-1H-imidazole.

$^1$H-NMR (CDCl$_3$): δ1.40 (t, 3H), 2.40 (s, 3H), 3.95 (bs, 2H), 4.40 (q, 4H), 7.70 (d, 1H), 7.25 (d, 1H), 7.75 (d, 2H), 7.35 (dd, 1H), 7.55 (s, 1H), 7.75 (s, 1H).

Step d. 2-Ethoxycarbonyl-8-(1-imidazolyl)-1-methylimidazo[1,2-a]quinoxalin-4(5H)-one A mixture of 1-(2-amino-5-(1-imidazolyl)phenyl)-4-ethoxycarbonyl-5-methyl-1H-imidazole (1.0 g, 3.2 mmol), 1,1'-carbonyldiimidazole (2.6 g, 16.0 mmol) in 1,2-dichlorobenzene (50 ml) was stirred at 180° C. for 16 h under N$_2$. The precipitate was filtered off and submitted to flash chromatography on silica gel 60 eluting with dichloromethane/methanol (4:1) to give 400 mg (37%) of the title compound. M.p. >250° C.

$^1$H-NMR (DMSO-d$_6$): δ1.35 (t, 3H), 3.25 (s, 3H), 4.35 (q, 2H), 7.15 (s, 1H), 7.50 (d, 1H), 7.75 (dd, 1H), 7.82, 8.25 (d, 1H), 8.30 (s, 1H).

EXAMPLE 28

2-Carboxy-8-(1-imidazolyl)-1-methylimidazo[1,2-a]quinoxalin-4(5H)-one

The title compound was prepared from 2-ethoxycarbonyl-8-(1-imidazolyl)-1-methylimidazo[1,2-a]quinoxalin-4(5H)-one (Example 27) following the procedure outlined in Example 4. M.p. >250° C.

$^1$H-NMR (DMSO-d$_6$): δ3.25 (s, 1H), 7.60 (d, 1H), 7.85 (dd, 1H), 8.00 (d, 1H), 8.35 (d, 1H), 8.45 (d, 1H), 9.80 (s, 1H), 12.20 (s, 1H).

EXAMPLE 29

2-Ethoxycarbonyl-1-diethoxyphosphoryl-7-trifluoromethylimidazo[1,2-a]quinoxalin-4(5H)-one 1-Bromomethyl-2-ethoxycarbonyl-7-trifluoromethylimidazo[1,2-a]quinoxalin-4(5H)-one (Example 3) (840 mg, 2.0 mmol) and triethyl phosphite (12 ml) was heated at 120° C. for 16 h. The mixture was concentrated in vacuo and the residue submitted to flash chromatography on silica gel, eluting with dichloromethane/methanol (9:1). The purified product was washed with ether to give 600 mg (63%) of the title compound. M.p. 198°–199° C.

$^1$H-NMR (DMSO-d$_6$): δ1.15 (t, 6H), 1.35 (t, 3H), 3.95 (m, 4H), 4.35 (q, 2H), 4.55 (d, 2H), 7.65 (d, 1H), 7.70 (s, 1H), 8.55 (s, 1H), 12.25 (s, 1H).

EXAMPLE 30

2-Ethoxycarbonyl-1-phosphonomethyl-7-trifluoromethylimidazo[1,2-a]quinoxalin-4(5H)-one To 2-Ethoxycarbonyl-1-diethoxyphosphoryl-7-trifluoromethylimidazo[1,2-a]quinoxalin-4(5H)-one (Example 29) (600 mg, 1.3 mmol) in acetonitrile (90 ml) was added bromotrimethylsilane (1.8 ml, 13.6 mmol) and the reaction mixture was heated at 40° C. for 16 h. The mixture was concentrated in vacuo and precipitated with water to give 520 mg (97%) of the title compound. M.p. >250° C.

$^1$H-NMR (DMSO-d$_6$): δ1.35 (t, 3H), 4.30 (m, 4H), 7.55 (d, 1H), 7.65 (s, 1H), 8.65 (d, 1H), 12.15 (s, 1H).

EXAMPLE 31

2-Carboxy-1-phosphonomethyl-7-trifluoromethylimidazo[1,2-a]quinoxalin-4(5H)-one

2-Ethoxycarbonyl-1-phosphonomethyl-7-trifluoromethylimidazo[1,2-a]quinoxalin-4(5H)-one (example 30) (210 mg, 0.5 mmol) in hydrobromic acid (48% in water) (20 ml) was stirred at 80° C. for 16 h. The mixture was concentrated in vacuo and the residue stirred with ether. The product, which was isolated by filtration was washed with cold water to afford 190 mg (97%) of the title compound. M.p. >250° C.

$^1$H-NMR (DMSO-d$_6$):

δ4.35 (m, 2H), 7.55 (d, 1H), 7.70 (s, 1H), 8.60 (d, 1H), 12.15 (s, 1H).

I claim:

1. A compound of formula I,

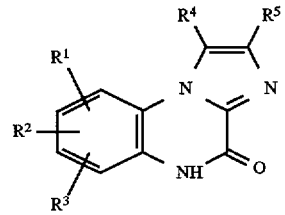

wherein $R^1$, $R^2$, $R^3$ independently are hydrogen, $C_{1-6}$-alkyl, $C_{1-6}$-alkoxy, halogen, $NO_2$, $NH_2$, $CF_3$ or $CN$;

$R^4$ is $CH_2$-$R^6$ wherein $R^6$ is halogen or $NR^7R^8$, wherein $R^7$ and $R^8$ independently are hydrogen,

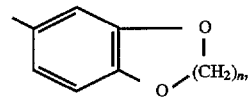

or $C_{1-6}$-alkyl optionally substituted with hydroxy or phenyl; wherein n is 1, 2 or 3; and $R^5$ is

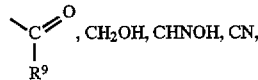, $CH_2OH$, $CHNOH$, $CN$,

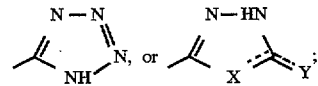;

wherein $R^9$ is hydroxy, $C_{1-6}$-alkoxy, hydrogen or $NR^{10}R^{11}$; $R^{10}$ and $R^{11}$ independently are hydrogen, $NH_2$ or $OH$; X is O or S; and Y is O or S when there is a double bond between Y and the carbon atom to which Y is attached and Y is $NH_2$ when there is a single bond between Y and the carbon atom to which Y is attached; or a pharmaceutically acceptable salt thereof.

2. A compound according to claim 1, wherein $R^4$ is bromomethyl.

3. A compound according to claim 1, wherein $R^6$ is $NR^7R^8$.

4. A compound according to claim 3, wherein $R^4$ is 3,4-methylenedioxyanilinomethyl or benzylaminomethyl.

5. A compound according to claim 3, wherein $R^1$, $R^2$, $R^3$ independently are hydrogen, Cl, Br, F or $CF_3$.

6. A compound according to claim 1, wherein $R^5$ is COOH; COOEt, $CH_2OH$, $CONH_2$, CHO, CH=NOH, $CONHNH_2$ or thioxo-oxadiazolyl.

7. A compound according to claim 1 which is

1-Bromomethyl-2-ethoxycarbonyl-7-trifluoromethylimidazo [1,2-a]quinoxalin-4(5H)-one;

1-Bromomethyl-2-carboxy-7-trifluoromethylimidazo [1,2-a]quinoxalin-4-(5H)one;

2-Ethoxycarbonyl-1-(3,4-methylenedioxyanilino)methyl-7trifluoromethylimidazo [1,2-a]quinoxalin-4(5H)-one;

2-Carboxyl-1-(3,4-methylenedioxyanilino)methyl-7-trifluoromethylimidazo [1,2-a]quinoxalin-4(5H)-one;

1-Benzylaminomethyl-2-ethoxycarbonyl-7-trifluoromethylimidazo [1,2-a]quinoxalin-4(5H)-one;

1-Benzylaminomethyl-2-carboxy-7-trifluoromethylimidazo[1,2-a]quinoxalin-4(5H)-one; or a pharmaceutically acceptable salt thereof.

8. A pharmaceutical composition comprising as active component a compound according to claim 1 a pharmaceutically acceptable carrier or diluent.

9. A pharmaceutical composition according to claim 8, wherein the compound is present in an amount in the range of 10–200 mg per unit dose.

10. A method of treating cerebral ischemia in a subject in need of such treatment comprising administering to the subject a neurologically effective AMPA antagonistic amount of a compound according to claim 1.

11. A method of treating cerebral ischemia in a subject in need of such treatment comprising administering to the subject a pharmaceutical composition according to claim 8.

12. A compound of formula I

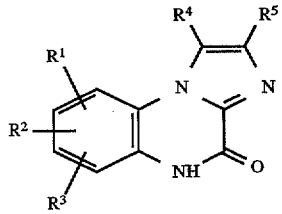

(I)

wherein $R^1$, $R^2$, $R^3$ independently are hydrogen, $C_{1-6}$-alkyl, $C_{1-6}$-alkoxy, halogen, $NO_2$, $NH_2$, $CF_3$, CN, $SO_2CH_3$, $SO_2CF_3$, $SO_2NR'R''$ or imidazolyl which is optionally substituted with phenyl or $C_{1-6}$-alkyl; wherein R' and R" independently are hydrogen or $C_{1-6}$-alkyl;

$R^4$ is $CH_2$-$R^6$ wherein $R^6$ is $POR'''R''''$, wherein R''' and R'''' independently are hydroxy or $C_{1-6}$-alkoxy; and $R^5$ is

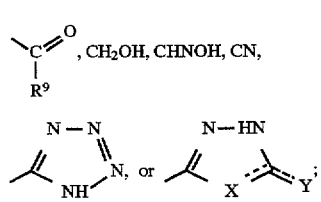

wherein $R^9$ is hydroxy, $C_{1-6}$-alkoxy, hydrogen or $NR^{10}R^{11}$; $R^{10}$ and $R^{11}$ independently are hydrogen, $NH_2$ or OH; X is O or S; and Y is O or S when there is a double bond between Y and the carbon atom to which Y is attached and Y is $NH_2$ when there is a single bond between Y and the carbon atom to which Y is attached; or a pharmaceutically acceptable salt thereof.

13. A compound according to claim 12, wherein $R^1$, $R^2$, $R^3$ independently are hydrogen, Cl, Br, F, $CF_3$, $SO_2CH_3$ or imidazolyl, optionally substituted with one or two of phenyl or methyl.

14. A compound according to claim 12, wherein $R^4$ is phosphonomethyl or diethoxyphosphoryl.

15. A compound according to claim 12, wherein $R^5$ is COOH; COOEt, $CH_2OH$, $CONH_2$, CHO, CH=NOH, $CONHNH_2$ or thioxo-oxadiazolyl.

16. A compound according to claim 12 which is

2-Ethoxycarbonyl-1-diethoxyphosphoryl-7-trifluoromethylimidazo[1,2-a]quinoxalin-4(5H)-one;

2-Ethoxycarbonyl-1-phosphonomethyl-7-trifluoromethylimidazo[1,2-a]quinoxalin-4(5H)-one;

2-Carboxy-1-phosphonomethyl-7-trifluoromethylimidazo[1,2-a]quinoxalin-4(5H)-one; or a pharmaceutically acceptable salt thereof.

17. A pharmaceutical composition comprising as active component a compound according to claim 12 a pharmaceutically acceptable carrier or diluent.

18. A pharmaceutical composition according to claim 17, wherein the compound is present in an amount in the range of 10–200 mg per unit dose.

19. A method of treating cerebral ischemia in a subject in need of such treatment comprising administering to the subject a neurologically effective AMPA antagonistic amount of a compound according to claim 12.

20. A method of treating cerebral ischemia in a subject in need of such treatment comprising administering to the subject a pharmaceutical composition according to claim 17.

21. A compound of formula I

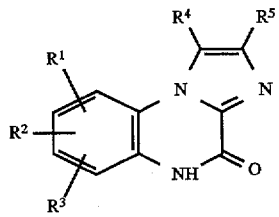

(I)

wherein $R^1$, $R^2$, $R^3$ independently are hydrogen, $C_{1-6}$-alkyl, $C_{1-6}$-alkoxy, halogen, $NO_2$, $NH_2$, $CF_3$, CN, $SO_2CH_3$, $SO_2CF_3$, $SO_2NR'R''$ or imidazolyl which is optionally substituted with phenyl or $C_{1-6}$-alkyl; wherein R' and R" independently are hydrogen or $C_{1-6}$-alkyl;

$R^4$ is $CH_2$-$R^6$ wherein $R^6$ is a piperazinyl or imidazolyl group which is optionally substituted with one or two of phenyl, $C_{1-6}$-alkyl or halogen;

$R^5$ is

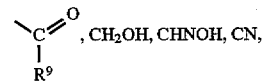

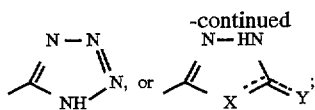

wherein $R^9$ is hydroxy, $C_{1-6}$-alkoxy, hydrogen or $NR^{10}R^{11}$; $R^{10}$ and $R^{11}$ independently are hydrogen, $NH_2$ or OH; X is O or S; and Y is O or S when there is a double bond between Y and the carbon atom to which Y is attached and Y is $NH_2$ when there is a single bond between Y and the carbon atom to which Y is attached; or a pharmaceutically acceptable salt thereof.

22. A compound according to claim 21, wherein $R^1$, $R^2$, $R^3$ independently are hydrogen, Cl, Br, F, $CF_3$, $SO_2CH_3$ or imidazolyl, optionally substituted with one or two of phenyl or methyl.

23. A compound according to claim 21, wherein $R^4$ is imidazolylmethyl optionally substituted with one or two of methyl or Cl; or piperazinylmethyl optionally substituted with methyl.

24. A compound according to claim 21, wherein $R^5$ is COOH; COOEt, $CH_2OH$, $CONH_2$, CHO, CH=NOH, $CONHNH_2$ or thioxo-oxadiazolyl.

25. A compound according to claim 21 which is

2-Ethoxycarbonyl-1-(1-imidazolylmethyl)-7-trifluoromethylimidazo[1,2-a]quinoxalin-4(5H)-one;

2-Carboxy-1-(1-imidazolylmethyl)-7-trifluoromethylimidazo[1,2-a]quinoxalin-4(5H)-one;

2-Ethoxycarbonyl-1-(2-methyl-1-imidazolyl)methyl-7-trifluoromethylimidazo[1,2-a]quinoxalin-4(5H)-one;

2-Carboxy-1-(2-methyl-1-imidazolyl)methyl-7-trifluoromethylimidazo[1,2-a]quinoxalin-4(5H)-one;

1-(4,5-Dichloro-1-imidazolyl)methyl-2-ethoxycarbonyl-7-trifluoromethylimidazo-[1,2-a]quinoxalin-4(5H)-one;

2-Carboxy-1-(4,5-dichloro-1-imidazolyl)methyl-7-trifluoromethylimidazo[1,2-a]quinoxalin-4(5H)-one;

2-Ethoxycarbonyl-1-(4-methyl-1-piperazinyl)methyl-7trifluoromethylimidazo[1,2-a]quinoxalin-4(5H)-one;

2-Carboxy-1-(4-methyl-1-piperazinyl)methyl-7-trifluoromethylimidazo[1,2-a]quinoxalin-4(5H)-one;

2-Carbazoyl-1-(1-imidazolylmethyl)-7-trifluoromethylimidazo[1,2-a]quinoxalin-4(5H)-one;

1-(1-Imidazolylmethyl)-2-(2(3H) thioxo-1,3,4-oxadiazol-5- yl) -7-trifluoromethylimidazo [1,2-a]quinoxalin-4(5H)-one;

2-Hydroxymethyl-1-(1-imidazolylmethyl)-7-trifluoromethylimidazo [1,2-a]quinoxalin-4(5H)-one;

2-Formyl-1-(1-imidazolylmethyl)-7-trifluoromethylimidazo[1,2-a]quinoxalin-4(5H)-one;

2-Hydroxyiminomethyl-1-(1-imidazolylmethyl)-7-trifluoromethylimidazo [1,2-a]quinoxalin-4(5H)-one; or a pharmaceutically acceptable salt thereof.

26. A pharmaceutical composition comprising as active component a compound according to claim 21 a pharmaceutically acceptable carrier or diluent.

27. A pharmaceutical composition according to claim 26, wherein the compound is present in an amount in the range of 10-200 mg per unit dose.

28. A method of treating cerebral ischemia in a subject in need of such treatment comprising administering to the subject a neurologically effective AMPA antagonistic amount of a compound according to claim 21.

29. A method of treating cerebral ischemia in a subject in need of such treatment comprising administering to the subject a pharmaceutical composition according to claim 26.

30. A compound of formula I

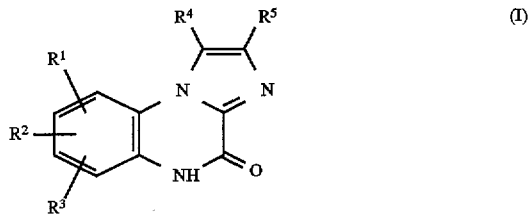

wherein at least one of $R^1$, $R^2$ and $R^3$ is $SO_2CH_3$, $SO_2CF_3$, or imidazolyl which is optionally substituted with phenyl or $C_{1-6}$-alkyl; and the other of $R^1$, $R^2$ and $R^3$ are independently one of these groups or hydrogen, $C_{1-6}$-alkyl, $C_{1-6}$-alkoxy, halogen, $NO_2$, $NH_2$, $CF_3$ or CN;

$R^4$ is hydrogen or $CH_2$-$R^6$ wherein $R^6$ is hydrogen, halogen or $NR^7R^8$, wherein $R^7$ and $R^8$ independently are hydrogen,

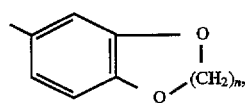

or $C_{1-6}$-alkyl optionally substituted with hydroxy or phenyl; wherein n is 1, 2 or 3; and $R^5$ is

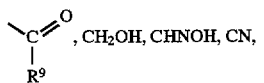, $CH_2OH$, CHNOH, CN,

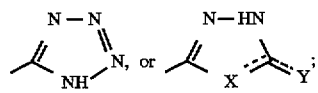

wherein $R^9$ is hydroxy, $C_{1-6}$-alkoxy, hydrogen or $NR^{10}R^{11}$; $R^{10}$ and $R^{11}$ independently are hydrogen, $NH_2$ or OH; X is O or S; and Y is O or S when there is a double bond between Y and the carbon atom to which Y is attached and Y is $NH_2$ when there is a single bond between Y and the carbon atom to which Y is attached; or a pharmaceutically acceptable salt thereof.

31. A compound according to claim 30, wherein $R^1$, $R^2$, $R^3$ independently are $SO_2CH_3$ or imidazolyl, optionally substituted with one or two of phenyl or methyl.

32. A compound according to claim 30, wherein $R^4$ is methyl, bromomethyl, 3,4-methylenedioxyanilinomethyl, or benzylaminomethyl.

33. A compound according to claim 30, wherein $R^5$ is COOH; COOEt, $CH_2OH$, $CONH_2$, CHO, CH=NOH, $CONHNH_2$ or thioxo-oxadiazolyl.

34. A compound according to claim 30 which is

2-Ethoxycarbonyl-1-methyl-7-methylsulfonylimidazo[1,2-a]quinoxalin-4(5H)one;

2-Carboxy-1-methyl-7-methylsulfonylimidazo[1,2-a]quinoxalin-4(5H)-one;

2-Ethoxycarbonyl-8-(1-imidazolyl)-1-methylimidazo[1,2-a]quinoxalin-4(5H)one;.

2-Carboxy-8-(1-imidazolyl)-1-methylimidazo[1,2-a]
 quinoxalin-4(5H)-one; or a pharmaceutically acceptable salt thereof.

35. A pharmaceutical composition comprising as active component a compound according to claim 30 a pharmaceutically acceptable carrier or diluent.

36. A pharmaceutical composition according to claim 35, wherein the compound is present in an amount in the range of 10–200 mg per unit dose.

37. A method of treating cerebral ischemia in a subject in need of such treatment comprising administering to the subject a neurologically effective AMPA antagonistic amount of a compound according to claim 30.

38. A method of treating cerebral ischemia in a subject in need of such treatment comprising administering to the subject a pharmaceutical composition according to claim 35.

* * * * *